United States Patent [19]

Adolph

[11] Patent Number: 4,997,499

[45] Date of Patent: Mar. 5, 1991

[54] BIS (DINITROPROPYL) FORMAL/DINITROBUTYL DINITROPROPYL FORMAL PLASTICIZER

[75] Inventor: Horst G. Adolph, Silver Spring, Md.

[73] Assignee: The United States of America as represented by the Secretary of the Navy, Washington, D.C.

[21] Appl. No.: 612,838

[22] Filed: May 22, 1984

[51] Int. Cl.$^5$ .............................................. C06B 25/00
[52] U.S. Cl. ..................................... 149/88; 568/590; 252/36.4
[58] Field of Search .......................... 149/88; 568/590; 252/364

[56] References Cited

U.S. PATENT DOCUMENTS

H,350 10/1987 Adolph et al. ........................ 149/88

| | | | |
|---|---|---|---|
| 2,967,195 | 1/1961 | Gold | 149/88 |
| 3,523,808 | 8/1970 | Gold et al. | 149/88 |
| 3,526,667 | 9/1970 | Hill et al. | 149/88 |
| 3,962,349 | 6/1976 | Adolph | 149/88 |
| 4,426,540 | 1/1984 | Shackelford et al. | 568/590 |
| 4,453,021 | 6/1984 | Adolph | 568/590 |

*Primary Examiner*—Edward A. Miller
*Attorney, Agent, or Firm*—Kenneth E. Walden; Roger D. Johnson

[57] ABSTRACT

A new compound 2,2-dinitrobutyl 2,2-dinitropropyl formal (DNBPF), $$CH_3C(NO_2)_2CH_2CH_2OCH_2OCH_2C(NO_2)_2CH_3,$$

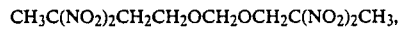

and a energetic plasticizer which is a 1:1 eutectic mixture of DNBPF and bis(2,2-dinitropropyl) formal.

2 Claims, No Drawings

BIS (DINITROPROPYL) FORMAL/DINITROBUTYL DINITROPROPYL FORMAL PLASTICIZER

BACKGROUND OF THE INVENTION

This invention relates to energetic plasticizers and more particularly to nitroalkyl energetic plasticizers.

BDNPF/A is a useful energetic (nitro)plasticizer of relatively low cost which has found application in propellant and explosive binders. BDNPF/A is a 1:1 eutectic mixture of bis(dinitropropyl)formal (BDNPF) and bis(dinitropropyl) acetal (BDNPA) BDNPB/A is an excellent plasticizer for polyurethanes, polyethylene glycols (PEG), and cellulose acetate butyrates (CAB); it has a low melting point (about 12° C.) and a low vapor pressure. A significant shortcoming of this material is the limited chemical and thermal stability of BDNPA. Thus, when heated separately at 150° C. in vacuo for 48 hours, BDNPF remains essentially unchanged whereas BDNPA decomposes to the extent of at least 30% with formation of new solid and liquid products which in turn undergo further decomposition. BDNPA is also more sensitive to acid hydrolysis than BDNPF. These undesirable properties of BDNPA are also exhibited by its eutectic mixture with BDNPF and adversely affect the utility of this plasticizer.

Therefore, it would be desirable to have a low cost energetic nitroplasticizer for use in propellant and explosive binders which is more chemically and thermally stable than BDNPF/A.

SUMMARY OF THE INVENTION

Accordingly, an object of this invention is to provide a new energetic nitro plasticizer for use in explosives and propellants.

Another object of this invention is to provide a new low cost energetic nitro plasticizer.

A further object of this invention is to provide a new energetic nitro plasticizer which has good chemical and thermal stability.

These and other objects of this invention are achieved by providing a new chemical compound 2,2-dinitrobutyl 2,2-dinitropropyl formal (DNBPF) and a new energetic plasticizer which is a 1:1 eutectic mixture of 2,2-dinitrobutyl 2,2-dinitropropyl formal and bis(2,2-dinitropropyl) formal (BDNPF).

A one step process of preparing the 1:1 eutectic mixture by contacting 2,2-dinitro-1-butanol, 2,2-dinitro-1-propanol, and formaldehyde in the presence of sulfuric acid is also provided.

The 1:1 molar mixture of 2,2-dinitrobutyl 2,2-dinitropropyl formal and bis(2,2-dinitropropyl) formal is useful as a plasticizer for propellant and explosive binders.

DETAILED DESCRIPTION OF THE PREFERRED EMBODIMENT

The present invention is based on a new compound 2,2-dinitrobutyl 2,2-dinitropropyl formal (DNBPF), $CH_3CH_2C(NO_2)_2CH_2OCH_2OCH_2C(NO_2)_2CH_3$.

DNBPF is prepared by the condensation of 2,2-dinitro-1-butanol and 2,2-dinitro-1-propanol with formaldehyde and sulfuric acid and is the main product of this reaction:

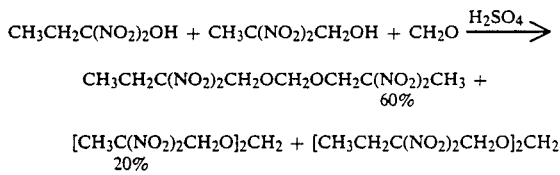

Pure DNBPF can be isolated from this mixture by column chromatography. The conditions for the reaction are illustrated by example 1.

2,2-dinitrobutyl 2,2-dinitropropyl formal has the same empirical formula $(C_8H_{14}N_4O_{10})$ as bis(2,2-dinitropropyl) acetal (BDNPA), $[CH_3C(NO_2)_2CH_2O]_2CHCH_3$. It also has approximately the same melting point (34°–6° C.) and the same density. 2,2-dinitrobutyl 2,2-dinitropropyl also forms a binary (1:1 molar) eutectic with bis(2,2-dinitropropyl) formal (BDNPF/DNBPF) which has approximately the same melting point as the binary (1:1 molar) eutectic of bis(2,2-dinitropropyl) acetal and bis(2,2-dinitropropyl) formal (BDNPF/A) which is used as a low cost energetic plasticizer.

There is, however, a critical difference between 2,2-dinitrobutyl 2,2-dinitropropyl formal and bis(2,2-dinitropropyl) acetal which goes to their relative usefulness in plasticizers. As discussed in the background of the invention, bis(2,2-dinitropropyl) acetal has poor chemical and thermal stability as compared to bis(2,2-dinitropropyl) formal. In contradistinction, 2,2-dinitrobutyl 2,2-dinitropropyl formal has a thermal stability which is essentially equal to that of bis(2,2-dinitropropyl) formal. This is demonstrated by the fact that after heating at 150° C. for 48 hours under vacuum, a sample of 2,2-dinitrobutyl 2,2-dinitropropyl formal shows no change. The bis(2,2-dinitropropyl) acetal breaks down and decomposes under those conditions. As a result, the new binary (1:1 molar) eutectic mixture of 2,2-dinitrobutyl 2,2-dinitropropyl formal and bis(2,2-dinitropropyl) formal offers a new low cost energetic plasticizer having a greatly improved thermal stability. The resistance to acid hydrolysis should also be better.

As a practiced matter, the 1:1 eutectic mixture of BDNPF and DNBPF is prepared in a single step as illustrated by example 2. Three moles of 2,2-dinitro-1-propanol and one mole of 2,2-dinitro-1-butanol are reacted with two moles of formaldehyde in the presence of sulfuric acid and cooling to produce the desired mixture. Preferably, from 70 to 100 percent sulfuric acid is used. The cooling is used to maintain the reaction temperature in the range of from -10° C. to 25° C.. The product mixture is composed of bis(2,2-dinitropropyl) formal, 2,2-dinitrobutyl 2,2-dinitropropyl formal, and bis(2,2-dinitrobutyl) formal in a molar ratio of 1:1:0.05, respectively. The small amount of bis(2,2-dinitrobutyl) formal present in the product does not interfere with the performance of the mixture as a thermally and chemically stable energetic plasticizer.

The 1:1 molar ratio of bis(2,2-dinitropropyl) formal (BDNPF) to 2,2-dinitrobutyl 2,2-dinitropropyl formal (DNBPF) is optional in that it produces the mixture with the lowest melting point. The ratio of BDNPF to DNBPF may be varied from 1:1 with a corresponding rise in the melting point; there is little if any advantage in doing so.

The general nature of the invention having been set forth, the following examples are presented as specific illustrations thereof. It will be understood that the invention is not limited to these examples but is susceptible to various modifications that will be recognized by one of ordinary skill in the art.

EXAMPLE 1

PREPARATION OF 2,2-DINITROBUTYL 2,2-DINITROPROPYL FORMAL

A mixture of 7.5g (0.05 moles) of 2,2-dinitro-1-propanol and 8.2g (0.05 moles) of 2,2-dinitro-1-butanol was added with cooling and stirring to a solution of 1.5g of paraformaldehyde (0.05 moles of formaldehyde) in 25 ml of 80% sulfuric acid. The mixture was stirred 20 hours at room temperature and extracted with 100 ml dichloromethane. The extract was washed with 100, 50, and 25 ml 0.1 N aqueous NaOH solution, dried ($MgSO_4$), filtered, and concentrated to give an oil weighting 13.5g. The mixture of formals was separated by repeated chromatography of silica gel with dichloromethane/hexane as eluant. Pure 2,2-dinitrobutyl 2,2-dinitropropyl formal was obtained in this fashion as an oil which soon crystallized; mp 34°–6° C. $^1$H NMR ($CDCl_3$):δ 1.07 (t,3H), 2.25 (s, 3H), 2.67 (q, 2H), 4.38 (s, 2H), 4.43 (s, 2H), 4.82 (s, 2H).

EXAMPLE 2

PREPARATION OF BDNPF/DNBPF MIXTURE (1:1)

A solution of 4.95 g (0.033 moles) 2,2-dinitro-1-propanol and 1.78g (0.011 moles) 2,2-dinitro-1-butanol in 10 ml dichloromethane was added with stirring to a solution of 0.66 g (0.022 moles) paraformaldehyde in 5.5 ml concentrated $H_2SO_4$. The mixture was stirred 15 minutes, the organic phase separated and the acid extracted once with 5 ml dichloromethane. The combined dichloromethane solution was washed with 0.2 N NaOH solution (3×20 ml), dried ($MgSO_4$), and freed from solvent to give 4.67 g of a colorless oil. NMR analysis (area ratio of O-$CH_2$-O to C-$CH_2$C peaks) show this to be a 1:1 mixture of bis(2,2-dinitropropyl) formal and 2,2-dinitrobutyl 2,2-dinitropropyl formal.

Numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. An energetic plasticizer comprising a mixture of bis(2,2-dinitropropyl) formal and 2,2-dinitrobutyl 2,2-dinitropropyl formal.

2. The plasticizer of claim 1 which is approximately a 1:1 molar binary eutectic mixture of bis(2,2-dinitropropyl) formal and 2,2-dinitrobutyl 2,2-dinitropropyl formal.

* * * * *